United States Patent [19]

Misumi et al.

[11] 4,239,686

[45] Dec. 16, 1980

[54] PROCESS FOR PRODUCING PHTHALIMIDO DERIVATIVES

[75] Inventors: Teruyuki Misumi; Kyogo Tanaka, both of Yokohama; Osamu Okuno, Kamakura, all of Japan

[73] Assignee: Asahi Kasei Kogyo Kabushiki Kaisha, Tokyo, Japan

[21] Appl. No.: 962,639

[22] Filed: Nov. 21, 1978

[51] Int. Cl.$^3$ ............................................. C07D 209/50
[52] U.S. Cl. ............................................. 260/325 PH
[58] Field of Search ........................ 260/325PH, 326.1

[56] References Cited

U.S. PATENT DOCUMENTS

| 2,964,533 | 12/1960 | von der Crone | 260/325 PH |
| 2,973,358 | 2/1961 | Pugin | 260/240 |
| 2,973,369 | 2/1961 | Pugin | 260/325 PH |
| 3,887,581 | 6/1975 | Kinoshita et al. | 260/325 PH |

FOREIGN PATENT DOCUMENTS

| 0086989 | 3/1959 | Denmark | 260/326.1 |
| 0853237 | 11/1960 | United Kingdom . | |

*Primary Examiner*—Donald G. Daus
*Assistant Examiner*—M. C. Eakin

[57] ABSTRACT

A process for producing a 3-iminohaloisoindoline-1-one which comprises treating a halophthalodinitrile with ammonia and/or an organic amine together with hydrogen peroxide in a mixed reaction medium comprising water and an organic solvent.

18 Claims, No Drawings

PROCESS FOR PRODUCING PHTHALIMIDO DERIVATIVES

BACKGROUND OF THE INVENTION

1. Field of the Invention

This invention relates to a process for producing a 3-iminohaloisoindoline-1-one useful as an intermediate for preparing quality organic pigments having high purity, excellent fastness to light and good resistance to heat.

2. Description of the Prior Art

Many methods are known for producing a 3-iminohaloisoindoline-1-one by using a specific reactant and a specific starting material such as a halophthalimide, a halophthalic anhydride and a halo-phthalodinitrile. Such processes are described, for example, in Japanese Patent Publication Nos. 4488/59, 1643/61, 3826/61 and 4521/61 and U.S. Pat. No. 3,887,581.

Of these methods, the process of U.S. Pat. No. 3,887,581 is particularly attractive industrially because the process is conducted using mild reaction conditions and a readily available starting material. Further, the process of this patent is simpler than the other processes. More specifically, according to the process of U.S. Pat. 3,887,581 a halophthalodinitrile is hydrated in the presence of an alkali metal hydroxide, an alkaline earth metal hydroxide, or a compound forming such hydroxides at a temperature of 10° to 100° C. for a time of from 0.5 to 40 hours.

The product thus obtained is mainly an alkali metal salt or alkaline earth metal salt of the 3-iminohalogenoisoindoline-1-one. Accordingly, it is necessary to further hydrolyze the salt with an acid to obtain the 3-iminohaloisoindoline-1-one. Furthermore, the purity of the 3-iminohaloisoindoline-1-one and its salt obtained by such a process is disadvantageously insufficient for use as a starting material for preparing quality organic pigments, and the pigments prepared therefrom contain inseparable impurities, with the result that the pigments are inferior in the clearness and vividness of color. Clearness and vividness are, of course, important characteristics of coloring agents.

Extensive investigations have been made in order to avoid the above-described disadvantages, and to directly obtain a 3-iminohaloisoindoline-1-one having high purity in high yields from a halophthalodinitrile.

SUMMARY OF THE INVENTION

According to the present invention, a process is provided for producing a 3-iminohaloisoindoline-1-one which comprises treating a halophthalodinitrile with ammonia and/or an organic amine together with hydrogen peroxide in a mixed treatment medium of water and an organic solvent.

DESCRIPTION OF PREFERRED EMBODIMENTS

Suitable starting materials which can be employed in the process of the present invention are halophthalodinitriles having one to four halogen atoms, such as chlorine, bromine, or fluorine atoms, on their benzene ring.

Specific examples of suitable halophthalodinitriles include 3-chlorophthalodinitrile, 4-chlorophthalodinitrile, 3,4-, 3,5-, 3,6- or 4,5-dichlorophthalodinitrile, 3,4,5- or 3,4,6-trichlorophthalodinitrile, 3,4,5,6-tetrachlorophthalodinitrile, 3-bromophthalodinitrile, 3,4-, 3,5-, 3,6- or 4,5-dibromophthalodinitrile, 3,4,5- or 3,4,6-tribromophthalodinitrile, 3,4,5,6-tetrabromophthalodinitrile, 3-fluorophthalodinitrile, 3,4-, 3,5-, 3,6- or 4,5-difluorophthalodinitrile, 3,4,5- or 3,4,6-trifluorophthalodinitrole and 3,4,5,6-tetrafluorophthalodinitrile. Of these compounds, 3,4,5,6-tetrachlorophthalodinitrile is preferably employed for practical purposes.

In the present invention, ammonia and an organic amine can be used either individually or as a combination thereof.

The organic amines which can be used in this invention may be any organic amines and include, for example, primary, secondary or tetiary alkylamines, primary, secondary or tertiary arylamines, tetraalkylammonium hydroxides and tetraarylammonium hydroxides.

Specific examples of suitable organic amines include ethylamine, propylamine, amylamine, diethylamine, triethylamine, tripropylamine, ethylenediamine, diethylenetriamine, ethanolamine, tetraethylammonium hydroxide, aniline, N-ethylaniline, cyclohexylamine, hexamethyleneimine, pyridine and picoline. Of these organic amines, those which are soluble in the reaction medium of this invention are preferred.

The ammonia and/or the organic amine may be introduced to the treatment system of this invention in the form of either a gas, a liquid or a solution thereof.

In order to carry out the process of this invention it is essential that the ammonia and/or the organic amine be used together with hydrogen perioxide. If the treatment is conducted using only the ammonia and/or the organic amine, i.e., without hydrogen peroxide, the desired 3-iminohaloisoindoline-1-one cannot be obtained, as is shown in Comparative Example 3. Also if the treatment is conducted using only hydrogen peroxide, i.e., without the ammonia and/or the organic amine, the 3-iminohaloisoindoline-1-one cannot be obtained as is shown in Comparative Example 4.

The amounts of ammonia and/or organic amine and hydrogen peroxide which can be used in the process of the present invention are not particularly limited. Preferably both (1) the ammonia and/or organic amine and (2) the hydrogen peroxide are employed in amounts of at least 0.5 mole, and more preferably from about 1.0 mole to about 10 moles, per mole of halophthalodinitrile. If the amounts of the ammonia and/or organic amine and the hydrogen peroxide are less than about 0.5 mole each, sufficient yields of the desired product cannot be obtained. Amounts higher than 10 moles can be used but are economically undesirable.

According to the present invention it is essential to conduct the treatment in a mixed treatment medium of water and an organic solvent.

Appropriate organic solvents which can be employed in this invention are hydrophilic solvents which are miscible with water including alcohols such as methanol, ethanol, isopropanol and ethylene glycol; ketones such as acetone, methyl ethyl ketone and cyclohexanone; cyclic ethers such as tetrahydrofuran and dioxane; nitriles such as acetonitrile and propionitrile; formamides such as formamide and N,N-dimethylformamide; acetamides such as N,N-dimethylacetamide; sulfoxides such as dimethyl sulfoxide; phosphoramides such as hexamethylenephosphoramide; and hydrophobic solvents including aromatic hydrocarbons such as benzene, toluene, xylene and chlorobenzene; and halogenated hydrocarbons such as chloroform, carbon tetrachloride and tetrachloroethanes. Of these solvents, the hydrophilic solvents such as the alcohols, ketones and cyclic ethers are preferred.

The weight ratio of the water to the organic solvent which can be used in this invention typically ranges from about 80:20 to about 30:70. A preferred weight ratio ranges from about 70:30 to about 40:60. If the weight ratio thereof is outside the range of about 80:20 to about 30:70, the reaction will proceed, at least in some cases, but the rate of reaction is disadvantageously decreased.

The treatment temperature which can be used in the process of the present invention is about 10° C. to about 100° C., and preferably about 30° C. to about 80° C. The treatment pressure used in this invention may be atmospheric pressure or within the range of the vapor pressure of the treatment system under the treatment conditions selected.

The treatment period of time which be used in the process of this invention may be varied depending upon factors such as the treatment temperature employed, the amount of the halophthalodinitrile used, the mixed treatment medium selected and other factors. Generally, the treatment period of time is from a few minutes to several hours. A preferred time is from about 30 minutes to about 10 hours.

According to the process of the present invention, the 3-iminohaloisoindoline-1-one having high purity can be directly obtained in high yields. More specifically, the 3-iminohaloisoindoline-1-one becomes solid in the treating system at the end of the reaction, and can be easily separated in a pure form from the reaction mixture by filtration, followed by washing with an appropriate solvent such as water. Thus the pigments prepared by condensation reaction of the 3-iminohaloisoindoline-1-one of this invention with a polyamine such as p-phenylenediamine are purer than those prepared by using conventional 3-iminohaloisoindoline-1-one. Also the coloring agents prepared from the 3-iminohaloisoindoline-1-one of this invention have excellent chroma of color.

The following Examples are given to illustrate the present invention more specifically. However, it should be understood that the invention is in no way limited by these Examples. Unless otherwise indicated, all parts, percents and ratios are by weight.

EXAMPLE 1

To a mixed treatment medium of 70 parts of water and 30 parts of acetone were added 5.32 parts of 3,4,5,6-tetrachlorophthalodinitrile. After sufficiently stirring, 3 parts of a 28 percent aqueous ammonia solution and 6 parts of a 30 percent hydrogen peroxide solution were added to the mixture. The resultant mixture was stirred at 50° C. for 4 hours. The reaction mixture was cooled to 15° C. and suction-filtered. The cake thus obtained was thoroughly washed with water and dried under reduced pressure to give 5.32 parts of a white solid. The solid was identified as 3-imino-4,5,6,7-tetrachloroisoindoline-1-one by elemental analysis and infrared absorption spectral analysis. The purity of the solid was measured by a high speed liquid chromatography (manufactured by Water Associates Ltd.), and found to be 99.8 percent.

The solid thus obtained was boiled with p-phenylenediamine in dichlorobenzene in the presence of an acidic catalyst for several hours. The reaction mixture was cooled to 15° C., suction-filtered, washed with methanol and dried to give 5.55 parts of a reddish yellow raw pigment. The raw pigment was identified by elemental analysis and infrared absorption spectral analysis as bis(4,5,6,7-tetrachloroisoindoline-1-one-3-ylidene)-phenylenediamine-(1,4) of the formula (I),

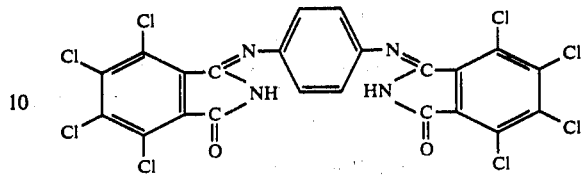

which correspond with bis(4,5,6,7-tetrachloroisoindoline-1-one-3-ylidene)phenylenediamine-(1,4) produced by a known method.

10 parts of the raw pigment thus obtained and 90 parts of sodium chloride were ball-milled with a cylindrical rod of SUS for 2 hours. The rod was separated from the mixture with a sieve and the sodium chloride was removed from the mixture by washing with water. The remainder of the mixture was dried to give the desired pigment as the final product. According to a conventional method, the pigment and linseed oil were kneaded by an automatic muller and coated on a glass plate. The color of the coating was clearer and more vivid than that of the coating obtained by Comparative Example 1.

COMPARATIVE EXAMPLE 1

In 12.5 parts of water, 5 parts of sodium hydroxide were dissolved and 75 parts of ethanol were added to the solution with sufficient stirring. To the solution, 10 parts of 3,4,5,6-tetrachlorophthalodinitrile was added. The mixture was stirred at a temperature of 70° C. to 78° C. for 5 hours. The reaction mixture was cooled to 15° C. and suction-filtered. The cake thus obtained was washed with water and then added to 100 parts of a 5 percent aqueous acetic acid solution. The mixture was stirred and suction-filtered, and the cake obtained was thoroughly washed with water and dried under reduced pressure to give 7.16 parts of a solid. The solid was identified as 3-imino-4,5,6,7-tetrachloroisoindoline-1-one. The purity was measured by the same high speed liquid chromatography as in Example 1 and was found to be 94.0 percent.

Using the 3-imino-4,5,6,7-tetrachloroisoindoline-1-one thus produced, a pigment and a plate coated with the pigment were prepared in the same manner as in Example 1.

The hue of the coating of this Comparative Example 1 was almost the same as that of the coating of Example 1, but the clearness and the vividness of color of the coating of this Comparative Example 1 were inferior to those of the coating of Example 1.

COMPARATIVE EXAMPLE 2

The same procedure as in Comparative Example 1 was repeated except that the cake, after washing with water, was not added to the 5 percent aqueous acetic acid solution. As a result, 7.48 parts of a solid were obtained. The solid was identified, by elemental analysis and infrared absorption spectral analysis, as the sodium salt of 3-imino-4,5,6,7-tetrachloroisoindoline-1-one.

The solid thus obtained was boiled with p-phenylenediamine in glacial acetic acid for 3 hours. The reaction mixture was cooled to 15° C., suction-filtered, washed with water and dried to give 5.73 parts of a reddish yellow raw pigment. The raw pigment thus obtained was identified, by infrared absorption spectral analysis, as being the same as the compound of formula I in Example 1. The yield of this condensation reaction was 73 mole percent.

In the same manner as in Example 1 a coating was prepared. The color of the coating was inferior in chroma to that of the coating obtained in Example 1.

EXAMPLE 2

To a mixed treatment medium of 50 parts of water and 50 parts of isopropanol were added 5.32 parts of 3,4,5,6-tetrachlorophthalodinitrile. This was followed by a further addition, with stirring, of 5.1 parts of triethylamine and 6 parts of a 30 percent aqueous hydrogen peroxide solution. The mixture was stirred at 80° C. for one hour, and then cooled to 20° C. The reaction mixture was suction-filtered and the cake obtained was thoroughly washed with water and dried under reduced pressure to give 4.91 parts of 3-imino-4,5,6,7-tetrachloroisoindoline-1-one. The purity was measured by the same high speed liquid chromatography as in Example 1 and was found to be 99.6 percent.

EXAMPLE 3

To a mixed treatment medium of 64 parts of water and 96 parts of dioxane were added 8.0 parts of 3,4,5,6-tetrachlorophthalodinitrile, 5.5 parts of diethylamine, and 3.5 parts of a 30 percent aqueous hydrogen peroxide solution. The mixture was stirred at 50° C. for 3 hours. The reaction mixture was treated in the same manner as in Example 2 to give 6.24 parts of 3-imino-4,5,6,7-tetrachloroisoindoline-1-one. The purity was measured in the same high speed liquid chromatography as in Example 1 and was found to be 99.3 percent.

EXAMPLE 4

50 parts of acetone were mixed with 76 parts of a 0.29 N aqueous tetraethylammonium hydroxide solution, followed by the addition of 5.32 parts of 3,4,5,6-tetrachlorophthalodinitrile and 6 parts of a 30 percent aqueous hydrogen peroxide solution. The mixture was stirred at 30° C. for 6 hours. The reaction mixture was treated in the same manner as in Example 2 to give 4.68 parts of 3-imino-4,5,6,7-tetrachloroisoindoline-1-one. The purity was measured by the same high speed liquid chromatography as in Example 1 and was found to be 99.6 percent.

EXAMPLE 5

To a mixed treatment medium of 64 parts of water and 36 parts of acetone were added, with stirring, 10.6 parts of 3,4,5,6-tetrachlorophthalodinitrile. To the resultant mixture were added 12 parts of a 28 percent aqueous ammonia solution and 24 parts of a 30 percent aqueous hydrogen peroxide solution. The mixture was stirred at 40° C. for 3 hours. The reaction mixture was treated in the same manner as in Example 2 to give 10.3 parts of 3-imino-4,5,6,7-tetrachloroisoindoline-1-one. The yield and purity measured by the same high speed liquid chromatography as in Example 1 were 90 mole percent and 99.7 percent, respectively.

EXAMPLE 6

To a mixed treatment medium of 39 parts of water and 40 parts of acetonitrile were added 6 parts of 3,6-dichlorophthalodinitrile, and the mixture was heated to 50° C. with stirring. This was followed by the addition of 10.4 parts of a 28 percent aqueous ammonia solution and 19.3 parts of a 30 percent aqueous hydrogen peroxide solution. The mixture was stirred at 50° C. for 2 hours. The reaction mixture was treated in the same manner as in Example 2 to give a solid identified as 3-imino-4,7-dichloroisoindoline-1-one by elemental analysis and infrared absorption spectral analysis. The yield and the purity measured by the same high speed liquid chromatography as in Example 1 were 85 mole percent and 99.7 percent, respectively.

EXAMPLE 7

To a mixed treatment medium of 70 parts of water and 30 parts of N,N-dimethylformamide were added 3.25 parts of 4-chlorophthalodinitrile, and the mixture was maintained, with sufficient stirring, at 30° C. Three parts of propylamine and 6 parts of a 30 percent hydrogen peroxide solution were added and the mixture was stirred at 30° C. for 6 hours. The reaction mixture was treated in the same manner as in Example 2 to give a solid identified as 3-imino-5-chloroisoindoline-1-one by elemental analysis and infrared absorption spectral analysis. The yield and the purity measured by the same high speed liquid chromatography as in Example 1 were 78 mole percent and 99.8 percent, respectively.

EXAMPLE 8

To a mixed treatment medium of 60 parts of water and 40 parts of acetone were added 8.88 parts of 3,4,5,6-tetrabromophthalodinitrile, and the mixture was heated, with stirring, to 60° C. Six parts of a 30 percent aqueous hydrogen peroxide solution and 3 parts of a 28 percent aqueous ammonia solution were added and the mixture was stirred at 60° C. for 2 hours. The reaction mixture was treated in the same manner as in Example 2 to give a solid identified as 3-imino-4,5,6,7-tetrabromoisoindoline-1-one by elemental analysis and infrared absorption spectral analysis. The yield and the purity measured by the same high speed liquid chromatography as in Example 1 were 89 mole percent and 99.2 percent, respectively.

EXAMPLE 9

To a mixed treatment medium of 60 parts of water and 40 parts of acetone were added 4 parts of 3,4,5,6-tetrafluorophthalodinitrile, and the mixture was heated to 60° C. with stirring. Six parts of a 30 percent aqueous hydrogen peroxide and 3 parts of a 28 percent aqueous ammonia solution were added and the mixture was stirred at 60° C. for 2 hours. The reaction misture was treated in the same manner as in Example 2 to give a solid identified as 3-imino-4,5,6,7-tetrafluoroisoindoline-1-one by elemental analysis and infrared absorption spectral analysis. The yield and the purity measured by the same high speed liquid chromatography as in Example 1 were 91 mole percent and 99.5 percent, respectively.

COMPARATIVE EXAMPLE 3

To a mixed treatment medium of 70 parts of water and 30 parts of acetone were added 5.32 parts of 3,4,5,6-tetrachlorophthalodinitrile, and the mixture was heated to 50° C. with stirring. Three parts of a 28 percent aqueous ammonia solution were added and the mixture was stirred at 50° C. for 4 hours. The reaction mixture was treated in the same manner as in Example 2. The formation of 3-imino-4,5,6,7-tetrachloroisoindoline-1-one was not observed by elemental analysis and infrared absorption spectral analysis, the solid recovered being mostly unreacted 3,4,5,6-tetrachlorophthalodinitrile.

COMPARATIVE EXAMPLE 4

The same procedure as in Comparative Example 3 was repeated except that 6 parts of a 30 percent hydrogen peroxide solution was used instead of the 3 parts of a 28 percent aqueous ammonia solution. By elemental analysis and infrared absorption spectral analysis of the solid thus produced, the formation of 3-imino-4,5,6,7-tetrachloroisoindoline-1-one was not observed, with the solid recovered being mostly unreacted 3,4,5,6-tetrachlorophthalodinitrile.

While the invention has been described in detail and with reference to specific embodiments thereof, it will be apparent to one skilled in the art that various changes and modifications can be made therein without departing from the spirit and scope thereof.

What is claimed is:

1. A process for producing a 3-iminohaloisoinodoline-1-one which comprises treating a halophthalodinitrile with
   (a) a reagent selected from the group consisting of ammonia, an organic amine, or mixtures thereof, and
   (b) hydrogen peroxide,
in a treatment medium comprising a mixture of water and water-miscible organic solvent.

2. The process of claim 1, wherein the halophthalodinitrile is a mono-, di-, tri- or tetra-halophthalodinitrile and the halogen atom is chlorine, bromine or fluorine.

3. The process of claim 2, wherein the halophthalodinitrile is mono-, di-, tri- or tetra-chlorophthalodinitrile.

4. The process of claim 3, wherein the halophthalodinitrile is 3,4,5,6-tetrachlorophthalodinitrile.

5. The process of claim 1, wherein the halophthalodinitrile is treated with ammonia and hydrogen peroxide.

6. The process of claim 1, wherein the halophthalodinitrile is treated with an organic amine and hydrogen peroxide.

7. The process of claim 1, wherein the amount of the reagent selected from the group consisting of ammonia, organic amine, or mixtures thereof is at least about 0.5 mole per mole of the halophthalodinitrile.

8. The process of claim 1, wherein the amount of the reagent selected from the group consisting of ammonia, organic amine, or mixtures thereof ranges from about 1.0 to about 10.0 mole per mole of the halophthalodinitrile.

9. The process of claim 1, wherein the amount of the hydrogen peroxide is at least about 0.5 mole per mole of the halophthalodinitrile.

10. The process of claim 9, wherein the amount of the hydrogen peroxide ranges from about 1.0 to about 10.0 moles per mole of the halophthalodinitrile.

11. The process of claim 1, wherein the weight ratio of the water to the water-miscible organic solvent in the treatment medium ranges from about 80:20 to about 30:70.

12. The process of claim 11, wherein the weight ratio of the water to the water-miscible organic solvent in the treatment medium ranges from about 70:30 to about 40:60.

13. The process of claim 1, wherein the organic amine is a primary, secondary or tertiary alkylamine, a primary, secondary or tertiary arylamine, a tetraalkylammonium hydroxide, or a tetraarylammonium hydroxide.

14. The process of claim 13, wherein the organic amine is triethylamine, diethylamine, propylamine or tetraethylammonium hydroxide.

15. The process of claim 1, wherein the water-miscible organic solvent is an alcohol, a ketone, a cyclic ether, a nitrile, a formamide, an acetamide, a sulfoxide or a phosphoramide.

16. The process of claim 15, wherein the water-miscible organic solvent is ethanol, ispropanol, acetone, dioxane, acetonitrile or N,N-dimethylformamide.

17. The process of claim 1, wherein the treating temperature ranges from about 10° C. to about 100° C.

18. The process of claim 17, wherein the treating temperature ranges from about 30° C. to about 80° C.

* * * * *

UNITED STATES PATENT AND TRADEMARK OFFICE
CERTIFICATE OF CORRECTION

PATENT NO. : 4,239,686

DATED : December 16, 1980

INVENTOR(S) : Teruyuki Misumi; Kyugo Tanaka, Kazuo Kabashima; and Osamu Okuno

It is certified that error appears in the above-identified patent and that said Letters Patent are hereby corrected as shown below:

On the cover page, in the designation of the Inventors, after "Misumi;" change "Kyogo" to --Kyugo--; and after "Tanaka,", delete "both" and insert --Kazuo Kabashima, all--.

Claim 16, line 39, change "ispropanol" to --isopropanol--.

Signed and Sealed this

Nineteenth Day of May 1981

[SEAL]

Attest:

RENE D. TEGTMEYER

Attesting Officer

Acting Commissioner of Patents and Trademarks